US00PP10450P

United States Patent [19]

Zary

[11] Patent Number: Plant 10,450

[45] Date of Patent: Jun. 16, 1998

[54] FLORIBUNDA ROSE PLANT NAMED 'JACURP'

[75] Inventor: Keith W. Zary, Thousand Oaks, Calif.

[73] Assignee: Bear Creek Gardens, Inc., Medford, Oreg.

[21] Appl. No.: 800,675

[22] Filed: Feb. 14, 1997

[51] Int. Cl.[6] ..... A01H 5/00

[52] U.S. Cl. ..... Plt./29

[58] Field of Search ..... Plt./22, 27, 28, Plt./29

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class, having unique purple-red flower color; blooms presented in clusters of 3 to 5 flowers; long vase life; and moderate production as a greenhouse cut flower spray rose.

1 Drawing Sheet

The present invention relates to a new and distinct variety of rose plant of the floribunda class which was originated by me by crossing the variety INTERprince, U.S. Plant Pat. No. 8,102, with the variety JACpurr, not patented.

The primary objective of this breeding was to produce a new rose variety having the clustered and well-formed flowers of the female parent combined with the rich purple color of the male parent. The objective was substantially achieved, along with other desirable improvements, as evidenced by the following unique combination of characteristics that are outstanding in the new variety and that distinguish it from its parents, as well as from all other varieties of which I am aware:

1. Unique purple red flower color;
2. Blooms presented in clusters of 3–5 flowers;
3. Long vase life;
4. Moderate production as a greenhouse cut flower spray rose.

Asexual reproduction of this new variety by budding, as performed at Wasco, Calif., shows that the foregoing and all other characteristics and distinctions come true to form and are established and transmitted through succeeding propagations.

the accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—INTERprince.

*Pollen parent.*—JACpurr.

Classification:

*Botanical.*—*Rose hybrida.*

*Commercial.*—Floribunda.

Flower

Observations made from specimens grown in a greenhouse environment at Somis, Calif. from March 1996 to January 1997.

Blooming habit: Recurrent.

Bud:

*Size.*—1-inch long when the petals start to unfurl.

*Form.*—The bud form is short, blunt.

*Color.*—When sepals first divide, bud color is Red-Purple Group 59C. When half brown, the upper sides of the petals are Red-Purple Group 59C; and the lower sides of the petals are Red-Purple Group 59C.

*Sepals.*—Color: Green Group 139C. Surface texture: Covered in fine hairs. There are three lightly appendaged sepals. There are two unappendaged sepals with hairy edges.

*Receptacle.*—Color: Green Group 139C. Shape: Apple. Size: Broad (¼ inch ×⅜ inch). Surface: Smooth.

*Peduncle.*—Length: Medium to short (1¾ to 2 inches). Surface: Smooth. Color: Medium green. Strength: Stiff, erect.

Bloom:

*Size.*—Small. Average open size is 2 to 2¼ inches.

*Borne.*—Several together, in clusters (3 to 5 flowers). If in clusters: Slightly rounded.

*Stem.*—Medium, Strong. Average length is about 18 to 22 inches.

*Form.*—When first open: High centered. Permanence: Flattens; outer petals curl back.

*Petalage.*—Number of petals under normal conditions: 35 to 40.

*Color.*—The upper sides of the petals are Red-Purple Group 59C. The reverse sides of the petals are Red-Purple Group 59C. The base of each petal has a small (¼×¼ inch) whitish half-moon at the point of attachment. The major color on the upper side is Red-Purple Group 59C.

*Variegations.*—Guard petals have a white streak.

*Discoloration.*—The general tonality at the end of the first day: No change. At the end of the third day: No change. By day 5 on the plant, or day 7 in the vase, there is some fading to Red-Purple Group 59D.

*Fragrance.*—Slight.

Petals:

*Texture.*—Thick.

*Shape.*—Deltoid.

*Form.*—Tips slightly recurved.

*Arrangement.*—Imbricated, with a few small petaloids in the center.

*Persistence.*—Drop off cleanly.

*Lastingness.*—On the plant: Long (7 days). As a cut flower: Long (10 days).

Reproductive parts:

*Anthers.*—Size: Medium. Quantity: Many. Color: Yellow. Arrangement: Regular around styles, mixed with occasional petaloids.

*Filaments.*—Color: Light yellow with some light red in the upper half of each filament.

*Pollen.*—Color: Lemon yellow.

*Styles.*—Color: Light red.

*Stigmas.*—Color: Greenish white.

Form: Bush.

Growth: Vigorous, upright and branching. Height at one year in the greenhouse without pruning is 6 to 7 feet; width 3½ to 4 feet. Produces about 150 stems per square meter of greenhouse.

Foliage:

*Number of leaflets on normal mid-stem leaves.*—5 or 7.

*Size.*—Medium to large (6 inches by 4 inches).

*Quantity.*—Normal.

*Color.*—New foliage: Greyed-Orange Group 176B but quickly becoming green. Old foliage: Upper surface Green Group 139A; lower surface Green Group 139C.

Leaflets:

*Shape.*—Pointed oval.

*Texture.*—Upper side: Leathery.

*Edge.*—Serrated.

*Serration.*—Single, small.

*Petiole rachis.*—Color; Green (reddish when young).

*Petiole underside.*—Smooth, with occasional prickles.

*Stipules.*—Short; serratedand bearded (⅜ to ½ inch).

*Disease resistance.*—Susceptible to mildew under normal growing conditions at Somis, Calif. Not tested for rust or blackspot.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Medium (¼ inch), straight.

*Color when young.*—Green.

Small prickles:

*Quantity.*—On main stalks: None. On laterals: None.

I claim:

1. A new and distinct variety of rose plant of the floribunda class, substantially as herein shown and described, characterized particularly as to novelty by the unique combindation of its unique purple-red flower color; blooms presented in clusters of 3 to 5 flowers; long vase life; and moderate production as a greenhouse cut flower spray rose.

* * * * *

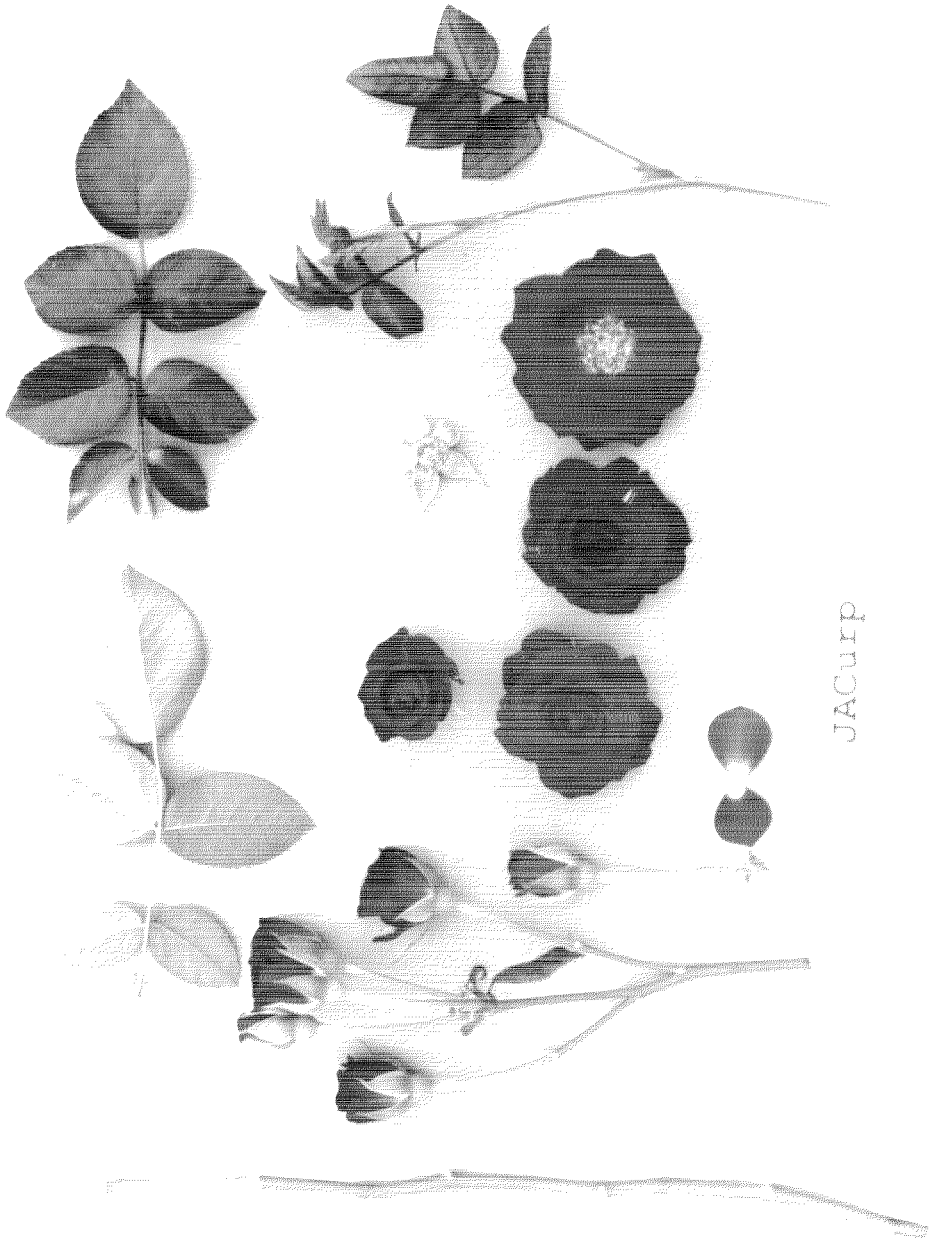
JACurp